United States Patent [19]

Pilgrim et al.

[11] Patent Number: 5,015,758

[45] Date of Patent: May 14, 1991

[54] PROCESS FOR THE PREPARATION OF 1-ADAMANTANE DERIVATIVES

[75] Inventors: William R. Pilgrim; Joel Lagiere, both of Valbonne, France

[73] Assignee: Centre International De Recherches Dermatologiques (CIRD), France

[21] Appl. No.: 403,280

[22] Filed: Sep. 6, 1989

[30] Foreign Application Priority Data

Sep. 7, 1988 [FR] France ................................ 88 11706

[51] Int. Cl.$^5$ .............................................. C07C 69/76
[52] U.S. Cl. ........................................ 560/56; 564/95; 568/62; 568/634; 568/732; 568/733; 568/737
[58] Field of Search .......................... 585/352; 560/56; 564/95; 568/62, 634, 732, 733, 737

[56] References Cited

U.S. PATENT DOCUMENTS 3,883,603  5/1975  Inamoto et al. .................. 560/56
4,087,410  5/1978  Dominianni et al. ............ 568/766

FOREIGN PATENT DOCUMENTS 0199636  4/1986  European Pat. Off. .

OTHER PUBLICATIONS

Journal of Medicinal Chemistry, vol. 18, No. 7, 1975, pp. 713–721, Washington, D.C., K. Aigami et al., "Biologically Active Polycycloalkanes". 1. Antiviral Adamantane Derivatives.

Primary Examiner—Paul J. Killos
Attorney, Agent, or Firm—Wegner, Cantor, Mueller & Player

[57] ABSTRACT

A process for the preparation of 1-adamantane derivatives characterized by the fact that a 1-acyloxyadamantane, in which the acyl group contains 1 to 4 carbon atoms, is reacted with a receptor compound in a linear aliphatic or cycloaliphatic type solvent in the presence of concentrated sulfuric acid and at ambient temperature.

11 Claims, No Drawings

PROCESS FOR THE PREPARATION OF 1-ADAMANTANE DERIVATIVES

This invention provides a new process for the preparation of 1-adamantane derivatives.

The 1-adamantyl radical is present in a number of active compounds having therapeutic activity, particularly as a substituent for aromatic compounds. The known synthetic methods capable of producing these compounds employ a haloadamantane as the initial product, especially 1-chloroadamantane or 1-bromoadamantane.

The major drawback of these processes is that they release large quantities of hydrochloric or hydrobromic acid. It is, however, possible to eliminate such release by adding metallic sodium or a base having a high amine content to the reaction medium, but in this case byproducts are produced.

The use of 1-adamantanol trifluoroacetate in excess, without catalyst or solvent, has also been proposed, but this method of synthesis is not always reproducible and its use cannot be generally applied for other types of aromatic compounds.

In addition, similarly to the process which involves haloadamantanes, byproducts are formed, particularly those of the 1,3-disubstituted adamantane type.

The presence of these byproducts makes these methods of synthesis particularly difficult to implement on an industrial scale.

Indeed, one cannot consider their elimination by chromatography and so purification processes by recrystallization must be used, resulting in a considerable effect on the production costs.

Furthermore, these recrystallizations are not always capable of eliminating all of the byproducts.

The present invention offers a new process for the preparation of 1-adamantane derivatives, and especially a process for adamantylation of aromatic compounds, in which the reaction takes place at ambient temperature without the release of dangerous gases. In addition, this new process reduces the reaction times and has the major advantage of keeping the formation of byproducts to a minimum and even eliminating them entirely.

The new process according to this invention provides 1-adamantane derivatives in a very pure form at an excellent rate of yield, to the extent that their isolation on an industrial level can be achieved by addition of a hydroxylated organic solvent, followed by filtration and a possible washing with water.

Although the process of the present invention is highly recommended for the adamantylation of aromatic compounds, it can also be applied to the preparation of other compounds in the 1-adamantane series.

The object of this invention is a process for the preparation of 1-adamantane derivatives. This process consists in causing a reaction between a 1-acyloxy adamantane, the acyl radical of which contains from 1 to 4 carbon atoms, with a receptor compound, with the reaction taking place at ambient temperature in solution in a solvent of the linear aliphatic or cycloaliphatic type, in the presence of concentrated sulfuric acid.

According to the invention, the 1-acyloxyadamantane is preferably 1-formyloxyadamantane, 1-acetoxyadamantane, or 1-propionyloxyadamantane.

The linear aliphatic solvent is preferably hexane, heptane, or octane, and the cycloaliphatic solvent is preferably cyclopentane, cyclohexane, or cyclooctane The proportion of solvent necessary to implement the process according to the invention is generally between 5 and 100 times the quantity of the 1-acyloxyadamantane used in the reaction and the proportion of concentrated sulfuric acid is generally between 0.1 and 0.5 part per part of 1-acyloxyadamantane.

According to a preferred method of implementation of the invention, the 1-acyloxyadamantane is prepared in situ by esterification of the 1-hydroxyadamantane or 1-adamantanol with an acid anhydride using concentrated sulfuric acid as the catalyst.

The carboxylic acid released during the esterification reaction does not have any adverse effect on the operation of the process of the invention.

The process according to the invention is more specifically intended for the adamantylation of aromatic compounds, and in this case the receptor compound can, for example, be anisole, phenol, toluene, naphthalene, thiophene, or furan and their substituted derivatives.

According to a preferred type of implementation, the aromatic receptor compound is:
4-bromoanisole
4-bromophenol
4-methoxybenzoic acid
methyl 4-methoxybenzoate
methyl 2-fluoro-4-methoxybenzoate
allyl 2-fluoro-4-hydroxybenzoate
methyl 6-(4-hydroxyphenyl)-2-naphthoate
methyl 6-(4-methoxyphenyl)-2-naphthoate
6-hydroxy-2-bromonaphthalene
6-methoxy-2-bromonaphthalene.

The receptor compound can also be a thiol, in which case the process according to this invention leads to the formation of an adamantyl thioether Among the thiols, special mention is made of 4-methoxybenzene thiol.

The receptor compound can also be a nitrile such as acetonitrile.

In this case the process according to the invention leads to the formation of an amide which can then be transformed under conventional conditions into 1-aminoadamantane (or 1-adamantanamine).

The following gives several non-limiting examples to illustrate the implementation of the process according to the invention.

EXAMPLE 1

Preparation of 2-(1-adamantyl)-4-bromo-1-methoxybenzene (a) From 1-acetoxyadamantane In a 100 ml three-necked flask are added, under nitrogen, 5 g of 1-acetoxyadamantane and 10 ml of n-heptane; after total solution, 1.26 g of concentrated sulfuric acid are added dropwise. At 20° C., 4.82 g of 4-bromoanisole are poured in and the mixture is agitated for 24 hours. Then, 60 ml of denatured ethanol are added and agitation is continued for 2 hours. The solid is filtered using sintered glass and then one dries in a vacuum oven at 20° C. for 24 hours; 5.67 g of expected raw product was collected. (Melting point: 144°–145° C.).

(b) From 1-adamantanol

In a ten-liter flask equipped with an agitation mechanism and a cooler are placed 750 g of 1-adamantanol and 2.4 l of n-heptane, under nitrogen. With good agitation, 18.3 g of concentrated sulfuric acid are slowly added and then 573.5 g of acetic anhydride. During the addition, the temperature rises from 21.C to approximately 37° C. Agitation is continued for 15 hours at approximately 21° C. and then 241.5 g of concentrated sulfuric acid are added. The temperature goes from 21° C. to 28° C. Once the temperature has returned to 21° C., 921.3 g of 4-bromoanisole are added and agitation is continued for 24 hours. 3 liters of denatured ethanol are added and one agitates for one hour. The solid product is collected by filtration and it is washed on the filter with 1 liter of absolute ethanol. After drying in a vacuum oven at 25° C. for 24 hours, one obtained 1.015 kg of desired raw product (Melting point: 142°–145° C.).

EXAMPLE 2

Preparation of 2-(1-adamantyl)-4-bromophenol

In a 100 ml three-necked flask, and under a nitrogen environment, is placed 1 g of 1-acetoxyadamantane and 10 ml of n-heptane. After total dissolution, 0.25 g of concentrated sulfuric acid is added drop by drop while keeping the temperature at 20° C., then 0.886 g of 4bromophenol is poured in slowly. After leaving 24 hours in vigorous agitation, 20 ml of denatured ethanol are added while maintaining the temperature at 20° C. Next, the solvent is evaporated to dryness under reduced pressure and a whitish raw product is obtained. The product is redissolved in water at approximately 60° C., it is washed to pH 6 and dried in a vacuum oven for 24 hours at 25° C. One collected 1.24 g of expected raw product (Melting point: 140°–141° C.).

EXAMPLE 3

Preparation of 3-(1-adamantyl)-4-methoxybenzoic acid

In a 100 ml three-necked flask, and under a nitrogen environment, are placed 1 g of 1-acetoxyadamantane and 50 ml of n-heptane. After dissolution, 0.25 g of concentrated sulfuric acid is added drop by drop at a temperature of approximately 22° C. and 0.783 g of 4-methoxybenzoic acid is poured in slowly. After leaving the mixture well agitated for 48 hours, 50 ml of denatured ethanol are added and the insoluble material is filtered Concentration of the filtrate volume to three quarters yields a solid white precipitate which is filtered with sintered glass. It is dried in a vacuum oven for 24 hours at 30° C. and 0.680 g of expected raw product was collected (Melting point: 245°–246° C.).

EXAMPLE 4

Preparation of methyl 3-(1-adamantyl)-4-methoxybenzoate

In a 100 ml three-necked flask, under a nitrogen environment, are placed 2 g of 1-acetoxyadamantane and 20 ml of n-heptane. After total dissolution, 0.5 g of concentrated sulfuric acid is added drop by drop. At a temperature of approximately 20.C, 1.71 g of methyl 4-methoxybenzoate is added slowly and agitated for 48 hours. The solid obtained is filtered with sintered glass and washed with water until neutrality is reached. After drying in a vacuum oven for 24 hours at 25 C, one recovered 2 g of expected raw product (Melting point: 136°–137° C.).

EXAMPLE 5

Preparation of methyl 5-(1-adamantyl)-2-fluoro-4methoxybenzoate

In a 100 ml flask, in a nitrogen atmosphere, are placed 2.48 g of I-adamantanol and 10 ml of n-heptane. Then 0.034 ml concentrated sulfuric acid and 1.76 ml of acetic anhydride are added dropwise. After one hour of agitation, there are added 0.87 ml of concentrated sulfuric acid and then a suspension of 2 g of methyl 2-fluoro-4-methoxybenzoate in 10 ml of cyclohexane. After 16 hours of reaction at room temperature, agitation is stopped and one separates the upper layer. The solvents heptane and cyclohexane are evaporated and then the product is extracted with dichloromethane. The organic phase is washed with aqueous bicarbonate solution, dried over magnesium sulfate and filtered on a Buchner funnel. After evaporation of the solvent under reduced pressure at 40° C., the product is dissolved in a 50:50 mixture of dichloromethane and hexane and then purified by filtration using a silica column. After passage of a liter of 50:50 dichloromethane/hexane eluent, one evaporates the solvents under reduced pressure at 30° C. and then dries the product in an oven at 50° C. for 24 hours. Thus were obtained 3 g of the pure product melting at 82°–88° C.

EXAMPLE 6

Preparation of allyl 3-(1-adamantyl)-2-fluoro-4hydroxybenzoate

In a 250 ml three-necked flask, under nitrogen, one introduces 3.04 g 1-adamantanol, 10 ml of n-heptane and 63 μl concentrated sulfuric acid. Dropwise, 2.16 ml of acetic anhydride are added and stirring is conducted for 3 hours at room temperature. Dropwise, 540 μl concentrated sulfuric acid are added and one adds portionwise 3.92 g of allyl 2-fluoro-4-hydroxybenzoate. After this addition, one adds 25 ml of dichloromethane and agitates at room temperature for 24 hours. After vacuum drying, the solid is taken up in water, neutralized to pH 7 with sodium bicarbonate and extracted with ethyl ether. The organic layer is washed with water and then with a concentrated aqueous sodium chloride solution. After drying over magnesium sulfate, one filters and evaporates the filtrate to obtain 7 g of crude product which is chromatographed on a silica column and eluted with dichloromethane. After trituration with hexane, filtration and drying in an oven at 50° C. there were obtained 3.86 g of the desired product, melting at 219°–222° C.

EXAMPLE 7

Preparation of methyl 6-[3-(1-adamantyl)-4-hydroxyphenyl-2-naphthoate

In a 100 ml three-necked flask, under a nitrogen environment, are placed 1 g of 1-acetoxyadamantane and 40 ml of n-heptane. After total solution, 0.25 g of concentrated sulfuric acid is added drop by drop. At 20° C., 1.43 g of methyl 6- (4-hydroxyphenyl)-2-naphthoate are poured in slowly and the mixture is left in vigorous agitation for 48 hours. After adding 40 ml of denatured ethanol and agitation for 2 hours, the solid is filtered and washed with heptane and then dried in a vacuum oven

EXAMPLE 8

Preparation of methyl 6-[3-(1-adamantyl)-4-methoxyphenyl]-2-naphthoate

In a 100 ml three-necked flask, are placed 1 g of 1-acetoxyadamantane and 50 ml of cyclohexane in a nitrogen environment. After total dissolution, 0.25 g of concentrated sulfuric acid is added drop by drop and 1 g of methyl 6-(4-methoxyphenyl)-2-naphthoate is added slowly. After leaving in vigorous agitation for 48 hours, 20 ml of denatured ethanol are added and the mixture is agitated for 2 hours. The solid obtained is filtered with sintered glass and washed abundantly with water until neutrality is reached. After drying at 30° C. for 24 hours in a vacuum oven, 1 g of desired raw product was obtained (Melting point: 221°–227° C.).

EXAMPLE 9

Preparation of 7-(1-adamantyl)-6-hydroxy-2-bromonaphthalene

In a 100 ml flask, under a nitrogen atmosphere, are placed 2 g of 1-acetoxyadamantane and 20 ml of n-heptane, and 0.5 g of concentrated sulfuric acid is introduced drop by drop. At a temperature of about 22.C, 2.3 of 6-hydroxy-2-bromonaphthalene are added slowly and the mixture is left in vigorous agitation. The solvent is eliminated by filtration and the solid residue in suspension in the water is collected. The residue is filtered and then washed until neutrality is obtained. The resulting reddish solid is washed again with hexane until a colorless filtrate is obtained. After drying in a vacuum oven for 24 hours at 30 C one obtains a raw product which is chromatographed with a silica column using an ethyl acetate and hexane mixture of 1:9 as the eluent. After evaporation of the solvents, 1.3 g of desired raw product were obtained (Melting point: 218°–224° C.).

EXAMPLE 10

Preparation of 7-(1-adamantyl)-6-methoxy-2-bromonaphthalene

In a 100 ml flask, under a nitrogen atmosphere, are placed 1 g of 1-acetoxyadamantane and 30 ml of n-heptane, and 0.25 g of concentrated sulfuric acid is introduced. At a temperature of about 20° C., 1.22 g of 2-bromo-6-methoxynaphthalene are poured in slowly and the mixture is left in vigorous agitation for 48 hours. Next, 20 ml of denatured ethanol are introduced and the mixture is evaporated to dryness under reduced pressure. The product is taken up in denatured ethanol and the precipitate is filtered with sintered glass. After drying of the raw product in a vacuum oven for 24 hours at 30° C., one purifies using silica column chromatography. There were obtained 0.4 g of the desired raw product (Melting point: 164°–168° C.).

EXAMPLE 11

Preparation of 2-(1-adamantyl)1-hydroxynaphthalene

A three-necked 100 ml flask is charged with 2.7 g of 1-acetoxyadamantane and 5 ml of cyclohexane in a nitrogen atmosphere. After complete dissolution, there are introduced 1.4 g of concentrated sulfuric acid. In a single portion there is added a suspension of 2 g of 1-naphthol in 15 ml of cyclohexane and one agitates for 45 minutes. 20 ml of ethanol are added and the mixture is filtered. One washes the residue with ethanol and with water and dries on the filter. After recrystallization with cyclohexane, one obtained 0.8 g of the desired product melting at 209.2°–209.6° C.

EXAMPLE 12

Preparation of (1-adamantyl)-4-methoxyphenyl sulfide

In a 100 ml three-necked flask, under a nitrogen environment, are placed 1 g of 1-acetoxyadamantane and 20 ml of n-heptane. After total dissolution, 0.25 of concentrated sulfuric acid is introduced dropwise. At a temperature of about 22.C, 0.63 ml of 4-methoxybenzenethiol is added using a syringe and it is left in vigorous agitation for 24 hours. Then, 20 ml of denatured ethanol are introduced and the mixture is concentrated under reduced pressure at 40° C. to obtain a raw product which is taken up in water. The product is then extracted using dichloromethane and the organic phase is washed with water until neutrality is reached. After evaporation of the organic phase, the residue is chromatographed using a silica column and a 1:4 mixture of dichloromethane and hexane as the eluent. After evaporation of the solvents, one obtains 1 g of desired raw product (Melting point: 70°–72° C.).

EXAMPLE I3

Preparation of 1-adamantyl-n-acetamide

Under a nitrogen atmosphere a 50 ml flask is charged with 1 g of 1-acetoxyadamantane and 10 ml of n-heptane. After complete solution, there are added dropwise 0.2 ml of concentrated sulfuric acid. At approximately 20° C., one adds dropwise 0.27 ml of acetonitrile and agitates for 24 hours. After filtration with a sintered glass filter, one recovers a white solid which is then placed in suspension in 20 ml of demineralized water. After agitation for 1 hour at room temperature, the product is filtered and dried in an oven at 60° C. for 24 hours. There were thus obtained 450 mg of desired product melting at 148°–150° C.

We claim:

1. A process for the preparation of 1-adamantane derivatives characterized by the fact that a 1-acyloxyadamantane, in which the acyl group contains 1 to 4 carbon atoms, is reacted with a receptor compound in a linear aliphatic or cycloaliphatic type solvent in the presence of concentrated sulfuric acid and at ambient temperature.

2. A process according to claim 1 wherein the 1-acyloxyadamantane is 1-formyloxyadamantane, 1-acetoxyadamantane, or 1-propionyloxyadamantane.

3. A process according to claim 1 wherein the linear aliphatic solvent is hexane, heptane, or octane.

4. A process according to claim 3 wherein the solvent is heptane.

5. A process according to claim 1 wherein the cycloaliphatic solvent is cyclopentane, cyclohexane, or cyclooctane.

6. A process according to claim 1 wherein the solvent is used in a proportion of between 5 and 100 times the quantity of the 1-acyloxyadamantane.

7. A process according to claim 1 wherein the concentrated sulfuric acid is used in a proportion of between 0.1:1 and 0.5:1 in relation to the quantity of 1-acyloxyadamantane.

8. A process according to claim 1 wherein the receptor compound is an aromatic compound of the group consisting of anisole, phenol, toluene, naphthalene, thiophene, or furan and their substituted derivatives.

9. A process according to claim 7 wherein the receptor is
4-bromoanisole
4-bromophenol
4-methoxybenzoic acid
4-methoxybenzoate
methyl 2-fluoro-4-methoxybenzoate
allyl 2-fluoro-4-hydroxybenzoate
methyl 6-(4-hydroxyphenyl)-2-naphthoate
methyl 6-(4-methoxyphenyl)-2-naphthoate or
6-hydroxy-2-bromonaphthalene.

10. A process according to claim 1 wherein the receptor compound is 4-methoxybenzene thiol.

11. A process according to claim 1 wherein the receptor compound is acetonitrile.

* * * * *